(12) United States Patent
Hajianpour

(10) Patent No.: US 10,357,295 B1
(45) Date of Patent: Jul. 23, 2019

(54) APPARATUS AND METHOD FOR CONNECTING OPPOSITE ENDS OF A SURGICAL WIRE WRAPPED AROUND AN INTERNAL BODY STRUCTURE

(71) Applicant: Mohammed A. Hajianpour, Fort Lauderdale, FL (US)

(72) Inventor: Mohammed A. Hajianpour, Fort Lauderdale, FL (US)

( * ) Notice: Subject to any disclaimer, the term of this patent is extended or adjusted under 35 U.S.C. 154(b) by 1233 days.

(21) Appl. No.: 14/023,076

(22) Filed: Nov. 13, 2013

(51) Int. Cl.
| | |
|---|---|
| *A61B 17/82* | (2006.01) |
| *A61B 17/84* | (2006.01) |
| *A61B 17/88* | (2006.01) |
| *B60P 7/08* | (2006.01) |
| *A61B 17/80* | (2006.01) |

(52) U.S. Cl.
CPC ............ *A61B 17/82* (2013.01); *A61B 17/842* (2013.01); *A61B 17/8076* (2013.01); *A61B 17/823* (2013.01); *A61B 17/8861* (2013.01); *A61B 17/8869* (2013.01); *B60P 7/083* (2013.01); *B60P 7/0823* (2013.01); *B60P 7/0838* (2013.01)

(58) Field of Classification Search
CPC . A61B 17/82; A61B 17/8861; A61B 17/8869; A61B 17/8076; A61B 17/808; A61B 17/823; A61B 17/842; A61B 17/8057; A61B 2017/681; B60P 7/0823; B60P 7/083; B60P 7/0838; B60P 7/0846; B60P 7/0853
USPC .... 606/74, 300, 324, 103, 86 A, 86 B, 86 R, 606/99, 117, 905, 139–141, 157, 158, 37; 140/123.5–123.6, 93 R, 93.2; 269/3, 6, 269/95; 254/245–246; 24/69 R, 115 R, 24/134 R, 133
See application file for complete search history.

(56) References Cited

U.S. PATENT DOCUMENTS

| | | | |
|---|---|---|---|
| 4,966,600 A | 10/1990 | Songer et al. | |
| 5,190,545 A | 3/1993 | Corsi et al. | |
| 5,312,410 A * | 5/1994 | Miller | A61B 17/8861 606/103 |
| 5,324,291 A | 6/1994 | Ries et al. | |
| 5,415,658 A | 5/1995 | Kupola et al. | |
| 5,607,430 A | 5/1997 | Bailey | |
| 5,720,747 A | 2/1998 | Burke | |
| 5,752,959 A * | 5/1998 | Korhonen | A61B 17/8869 606/103 |
| 6,605,091 B1 * | 8/2003 | Iwanski | A61B 17/82 606/74 |
| 8,062,344 B2 * | 11/2011 | Dorn | A61F 2/95 606/108 |
| 2004/0199169 A1 * | 10/2004 | Koons | A61B 17/8861 606/103 |

(Continued)

*Primary Examiner* — Eric S Gibson
*Assistant Examiner* — Marcela I Shirsat
(74) *Attorney, Agent, or Firm* — Ronald V. Davidge

(57) ABSTRACT

Opposite ends o a loop of surgical wire extending around an internal body part are joined by a connector, with the first end being rigidly fastened to the connector and with the second end then being pulled into place within a wire puller having a capstan that is rotated by squeezing a handle, preferably until the second end of the wire breaks, leaving one piece of wire in the wire puller and the other piece of the wire, extending to the loop, fastened within the connector. As the wire is tightened by the wire puller, a locking structure within the connector is deflected by contact with the tip of the wire puller into a shape preventing further movement off the wire within the connector.

9 Claims, 5 Drawing Sheets

(56) References Cited

U.S. PATENT DOCUMENTS

2013/0018375 A1* 1/2013 Dell'Oca ........... A61B 17/8869
606/74

* cited by examiner

APPARATUS AND METHOD FOR CONNECTING OPPOSITE ENDS OF A SURGICAL WIRE WRAPPED AROUND AN INTERNAL BODY STRUCTURE

RELATED APPLICATIONS

Not applicable.

FEDERALLY SPONSORED RESEARCH OR DEVELOPMENT

Not applicable.

BACKGROUND OF THE INVENTION

1. Field of the Invention

This invention relates to the internal fixation of bone fractures and, more particularly a method and apparatus for joining the ends of a surgical wire looped around an internal body structure, such as a bone.

2. Summary of the Background Information

The patent literature includes a number of descriptions of crimpable connectors for joining surgical wires, such as end portions of a loop of surgical wire, which are described along with specialized tools for crimping the connectors to hold the wires therein in place. For example, a method for securing body parts with a cable is described as using clamping pliers that comprise a pair of operating handles and connected, opposed jaws. The jaws define opposed recesses for carrying and crimping a tubular crimp member by manual pressure on the operating handles. A capstan is carried on one of the handles for winding a cable which passes through the tubular crimp member carried in the jaws.

The apparatus of another such example includes a pair of operating handles that are biased apart and that oppose a pair of opposed jaws to which they are connected. Disposed on opposite sides of the operating handles are a pair of capstans. The jaws are adapted to hold a crimp member therein without deforming it while opposite ends of a length of wire are passed through the crimping member in opposite directions. Each end of the wire is rapped about an associated capstan. A ratchet handle simultaneously rotates both capstans to wrap the opposite ends of the wire. Once the desired traction force has been achieved, the jaws are further activated to crimp the crimp member. A ring-shaped crimp member is also disclosed which has a central opening extending along the axis thereof and two parallel channels, one channel being disposed on either side of the central opening.

A surgical connector for cable is additionally described as comprising a body having a pair of opposed ends and a first side extending between the ends. Outwardly extending projections adjacent the first side and ends may be provided to facilitate securance of the connector in a desired position. Cable-receiving bores extend from each of the ends inwardly toward each other, typically at an obtuse angle of less than 1800. The bores have inner ends that communicate with a central aperture which is open to at least the side of the body which is opposed to the first side. Alternatively, the central aperture may extend entirely through the body and be open to both the first side and the opposed side. Also, a novel retention technique for cable is disclosed, for more general use, if desired.

An implant for use in reattaching a bone section following bone surgery is further described as including a plate-like member for fitting over at least a portion of the outer surface of the bone section to be reattached. The plate has an inner surface for engaging the bone section and an outer surface facing away from the bone section and side walls extending between the inner and outer surface. The outer surface includes at least one cable holding portion for holding a cable in place. A rectangular body receives the ends of a cable and allows for gripping and holding the cable under tension. The rectangular body has opposing concave sides and a pair of openings parallel to the concave sides for receiving the end of the cable. The rectangular body is collapsible by a crimping tool which pinches the cable in the openings. A recess extends across the outer surface of the plate-like member for receiving the rectangular body with the recess intersecting the cable holding portions.

SUMMARY OF THE INVENTION

According to one aspect of the invention, apparatus is provided, including a loop of surgical wire, a wire connector, and a wire puller. The loop of surgical wire is configured to be wrapped at least one time around an internal body structure. The wire connector includes a connector housing, a first receptacle configured to accept and hold a first end portion of the loop of surgical wire, and a second receptacle, configured to accept and hold a second end portion of the length of surgical wire. The second receptacle includes a locking structure allowing movement of the second end portion within the second receptacle with the locking structure in an unlocked condition and preventing movement of the second end portion within the second receptacle with the locking structure in a locked condition. The locking structure includes an external locking surface, wherein external pressure on the external locking surfaces causes the locking structure to change from the unlocked condition to the locked condition. The wire puller, which includes an external puller surface, is configured to pull the second end portion, extending from the second receptacle of the wire connector, while providing the external pressure on the external locking structure of the wire connector. For example, the first receptacle includes a pair of holes extending through the connector housing, with the first end portion being formed to extend through both of the holes within the first receptacle.

The second receptacle may additionally include a housing hole having an alignment axis within the connector housing, while the locking structure additionally includes a locking member having a locking hole and a flexible structure attaching the locking member to the connector housing, wherein the flexible structure is deflected to move the locking hole out of alignment with the housing hole by applying the external pressure to the external locking surface, changing the locking structure from the unlocked condition to the locked condition. Preferably, the locking structure includes an inner locking member having an inner locking hole, an inner flexible structure attaching the inner locking member to the connector housing, an outer locking member having an outer locking hole, and an outer flexible structure attaching the outer locking member to the inner locking member. The flexible structures are deflected to move the locking holes out of alignment with one another and with the housing hole by applying the external pressure to the external locking surface, changing the locking structure from the unlocked condition to the locked condition. For example, the first flexible member comprises a beam structure disposed in a transverse direction from the alignment axis, while the second flexible structure comprises a beam structure disposed opposite the transverse direction from the alignment axis. The external locking surface is then formed by an external surface of the outer locking member, extending around the outer locking hole.

The wire puller includes a puller housing and an elongated tubular member extending outward from the housing, with the external puller surface disposed at an end of the elongated tubular member for receiving the second end portion. The wire puller is configured to pull the second end portion through a hole within the external locking surface and a hole within the external puller surface with the external puller surface held in contact with the external locking surface. The wire puller additionally includes a capstan, with a wire channel extending from the hole within the external puller surface to the capstan, and a capstan drive. The capstan is configured for winding the second portion as it is pulled from the wire connector. The capstan drive is configured for rotating the capstan with a torque sufficient to push the external puller surface against the external locking surface with a force sufficient to cause the locking structure to change from the unlocked condition to the locked condition. Preferably, the capstan drive is additionally configured to produce a torque sufficient to bread the surgical wire within the second end portion. With the capstan being rotatably mounted on the housing, the capstan drive comprises a handle, a return spring, drive and braking ratchets, and drive and braking pawls. The handle is movably attached to the puller housing to move in either direction between an open position and a closed position. The return spring moves the handle from the closed position to the open position. The ratchets are each attached to the capstan, with the drive ratchet having teeth oriented to drive the capstan in a forward direction of rotation within the housing, and with the braking ratchet having teeth oriented to restrict rotation of the capstan within the puller housing in a direction opposite the forward direction. The drive pawl has a proximal end attached to the puller housing and a distal end held in contact with the teeth of the drive ratchet. The braking pawl has a proximal end attached to the puller housing and a distal end held in contact with the teeth of the braking ratchet. The apparatus may additionally include a capstan release member movable between an engaged position, allowing the distal end of the braking pawl to be held in contact with the teeth of the braking ratchet, and a disengaged position, holding the distal end of the braking pawl away from the teeth of the braking ratchet.

Preferably, the wire puller further includes a wire channel extending between the hole within the external puller surface and the capstan, with the capstan including a wire receiving slot, a removable wire retainer, and a wire ejection pin. The wire receiving slot extends inward from an outer end of the capstan. The removable wire retainer extends into the wire receiving slot to hold a wire within the slot. The wire ejection pin is movable into the wire retaining slot to push a wire outward from the slot. For example, the wire receiving slot may have a cruciform shape, with the capstan including a threaded hole extending inward from the outer end and a smooth hole extending inward from an end opposite the outer end. Then, the removable wire retainer comprises a screw engaging the threaded hole within the capstan, while the wire ejection pin is mounted to slide within the smooth hole in the capstan.

In accordance with a second aspect of the invention, a method is provided for winding a surgical wire around an internal body structure. The method includes: attaching a first end of the surgical wire to a first receptacle within a wire connector; forming at least one loop around the internal body structure with the surgical wire; moving the second end of the surgical wire into a wire puller; and operating the wire puller to continue pulling the second end of the surgical wire into the wire puller, with an external surface of the wire puller being pushed against an external surface of the second receptacle of the wire connector to move a locking member within the second receptacle into a locked position, preventing further movement of the second end portion within the second receptacle.

The method may additionally comprise operating the wire puller with the locking member in the locked position until the second of the surgical wire breaks in two. Alternately, the method may additionally comprise releasing operation of the wire puller to allow movement of the wire puller away from the wire connector, and cutting the surgical wire extending between the wire puller and the wire connector.

For example, the step of operating the wire puller may include repeatedly squeezing a handle to move the handle toward a housing while driving a capstan in a forward rotational direction, and repeatedly releasing the handle to be moved away from the housing by a return spring, with a braking mechanism preventing rotation of the capstan opposite the forward rotational direction.

In accordance with a third aspect of the invention, a wire connector is provided, including a connector housing and first and second receptacles. The first receptacle is configured to accept and hold a first end portion of a loop of surgical wire, while the second receptacle is configured to accept and hold a second end portion of the loop of surgical wire. The second receptacle includes a locking structure allowing movement of the second end portion within the second receptacle with the locking structure in an unlocked condition and preventing movement of the second end portion within the second receptacle with the locking structure in a locked condition. The locking structure includes an external locking surface, configured so that external pressure on the external locking surfaces causes the locking structure to change from the unlocked condition to the locked condition.

BRIEF DESCRIPTION OF THE DRAWINGS

These and other aspects of the invention will be made apparent by reading the following specification in conjunction with the accompanying figures, in which.

DETAILED DESCRIPTION OF THE INVENTION

Figure 1:
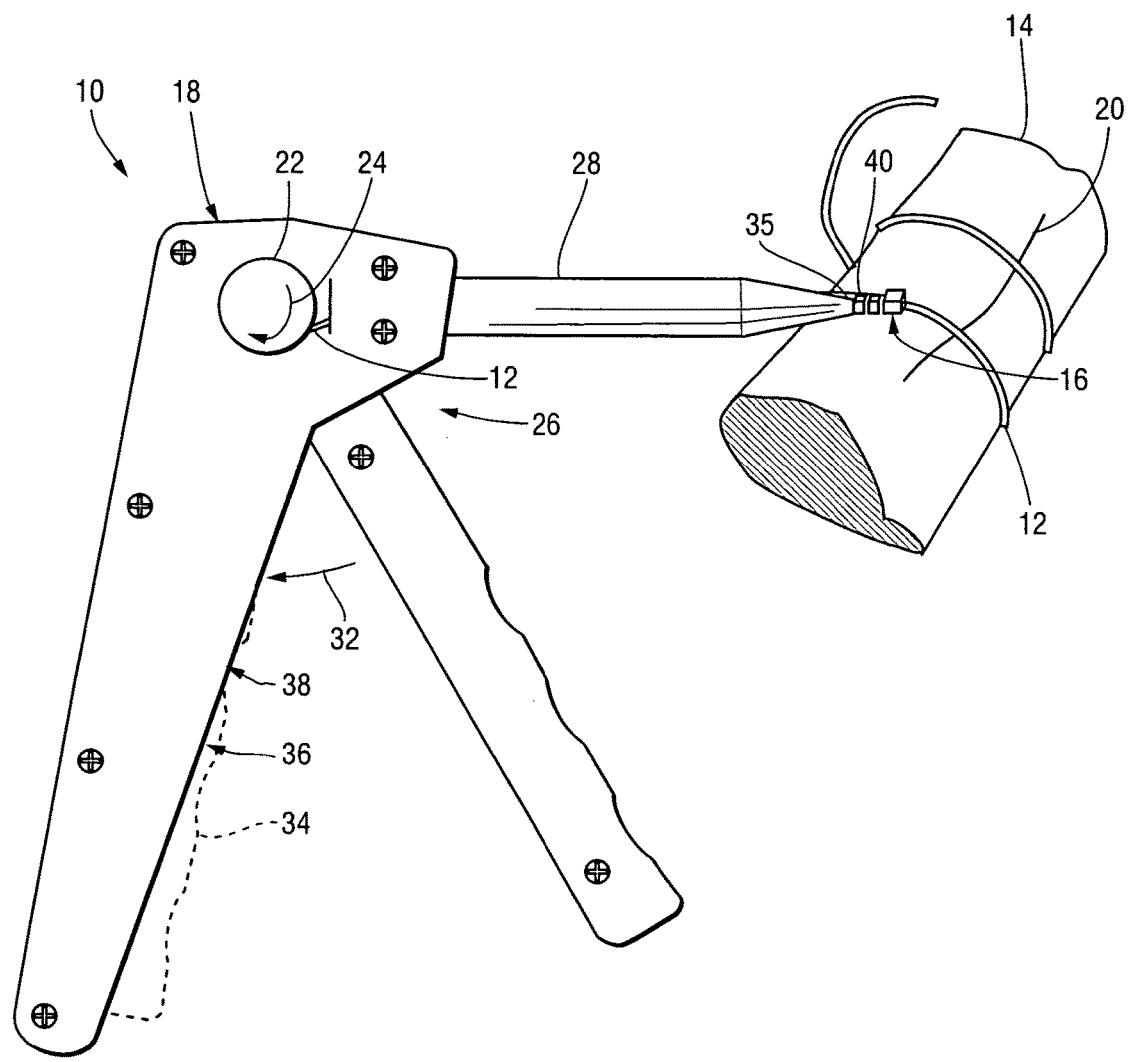
FIG. 1 is a perspective view of a wire apparatus built and used in accordance with a first embodiment of the invention.

FIG. 1 is a perspective view of wire apparatus 10 built and used in accordance with a first embodiment of the embodiment to include a surgical wire 12 wrapped one or more times around an internal body part, such as the bone 14, forming a loop 15, a wire connector 16, and a wire puller 18. The surgical wire 12 may be solid, stranded, or braided as a wire rope. For example, the wire apparatus 10 can be used in the internal fixation of a fracture 20 extending along the bone 14. The wire puller 18 includes a capstan 22, which is driven in rotation in the direction of arrow 24 by a capstan drive 26, storing a portion of the surgical wire 12 as it is pulled through an elongated tubular member 28. Specifically, the capstan drive 26 is operated to drive the capstan in rotation by, generally repeatedly, pivoting a handle 30 in the direction of arrow 32 between an open position, in which it is shown, and a closed position, in which it is induced by dashed lines 34, disposed partly within an opening 36 within a housing 38 The wire connector 16 includes a locking structure 40 that is moved from an unlocked condition to a locked position, in which the surgical wire 12 cannot slide within the locking structure 40, through contact with an external surface 35 at a tip of the elongated tubular member 28

Figure 2:
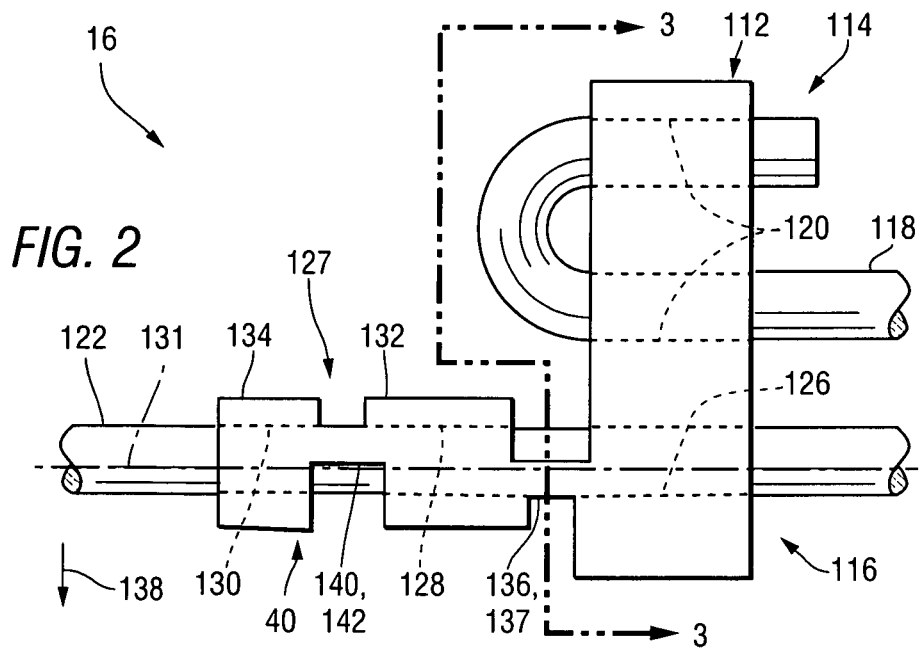
FIG. 2 is a plan view of a wire connector within the apparatus of FIG. 1, shown in an unlocked condition.
Figure 3:
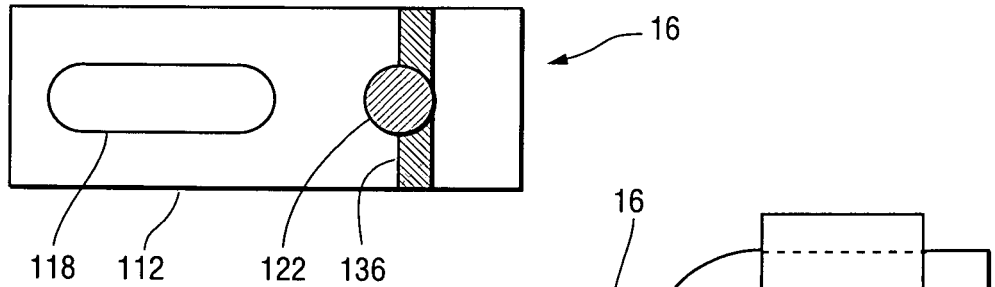
FIG. 3 is a cross-sectional elevation of the wire connector of FIG. 2, taken as indicated by section line 3-3 in FIG. 2.

FIG. 2 is a plan view of the wire connector 16, shown in an unlocked condition, while FIG. 3 is a cross-sectional elevation thereof, taken as indicated by section line 3-3 in FIG. 2. The wire connector 16 includes a connector housing 112, a first receptacle 114 and a second receptacle 116. The process of installing the wire apparatus 106 begins with installing a first end portion 118 of the loop 15 (shown in FIG. 1) of surgical wire 12 in the first receptacle 114 of the wire connector 16. For example, the first receptacle 114 includes a pair of holes 120 extending through the connector housing 112, with the first end portion 118 being locked in place within the first receptacle 114 by being formed to extend through both the holes 120. Next, the surgical wire 12 is wrapped as many times as needed around the bone 14, and a second end portion 122 of the surgical wire 12 is inserted through the second receptacle 116. The second receptacle 116 includes a housing hole 126 within the connector housing 112 and through a locking structure 127. Since the wire connector 16 is in the unlocked condition, with the housing hole 126, a first locking hole 128, and a second locking hole 130 aligned along a common axis 131, the second end portion 122 can be easily inserted and moved through these holes 126, 128, 130.

The locking structure 126 includes a first locking member 132, through which the first locking hole 123 extends, and a second locking member 134, through which the second locking hole 130 extends. The first locking member 132 is attached to the connector housing 112 by a first flexible member 136, which comprises a first beam structure 137 disposed from the common axis 131 in a transverse direction indicated by arrow 138, while the second locking member 134 is attached to the first locking member 132 by a second flexible member 140, which comprises a second beam structure 142 disposed from the common axis opposite the first transverse direction of arrow 138.

Figure 4:
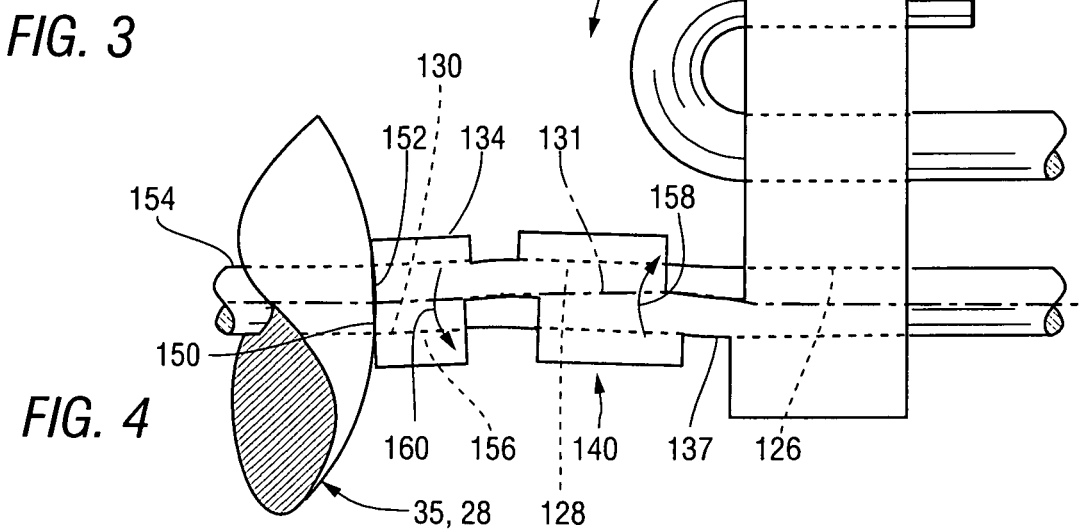
FIG. 4 is a plan view of a wire connector of FIG. 2, shown in a locked condition.

FIG. 4 is a plan view of the wire connector 16, shown in a locked condition following contact and pressure between an external locking surface 50 of the second locking member 134 and an external puller surface 152 at the tip 34 of the elongated tubular member 28. Specifically, since the surgical wire 12 is pulled through a hole 154 at the center of the external puller surface 152 and through a hole 156 at a center of the external locking surface 150, the action of winding the surgical wire 12 on the capstan 22 causes these surfaces 150, 152 to come together. Then, a continued effort to wind the surgical wire 12 on the capstan 22 generates a compressive force, acting along the common axis 131, between these surfaces 152, 156. Because the first beam structure 137 is disposed in the transverse direction of arrow 138 from the common axis 131, a bending moment resulting from the application of compression along the common axis 131 causes the first beam structure 137 to bend in the direction of arrow 158 and additionally causes the second beam structure 142 to bend in the direction of arrow 160. This bending results in permanent deformation so that the second end portion 122 is locked within the locking structure 126.

Thus, in accordance with the first embodiment of the invention, a method for winding a surgical wire 12 around an internal body structure, such as the bone 14, begins with attaching a first end of a loop 15 of the surgical wire 12 to the first receptacle 114 of the wire connector 16. This may be done during the surgical procedure, or a number of loops 15 of surgical wire 12 attached to the first receptacle 114 of a number of loops 15 may be previously prepared and supplied to the surgical procedure in sterile packages. Then, the surgical wire 12 is wrapped one or more times around the body structure, and the second end portion 122 of the loop 15 is moved through the second receptacle 116 of the wire connector 16 and into the wire puller 18. The wire puller 18 is then operated, with the second end portion 122 being wrapped around the capstan 22, which is turning in the forward direction of arrow 24, bringing the external surface 150 within the second receptacle 114 of the wire connector 16 into contact with the external surface 35 of the wire puller 18. As these external surfaces 150, 35 are held together, deflections within the second receptacle 118 bring holes 126, 128, 130 within the second receptacle 118 out of alignment with one another, preventing further movement of the second end portion 122 within the second receptacle 118. The operation of the wire puller 18 is then continued until the second end portion 118 breaks into two pieces.

Figure 5:
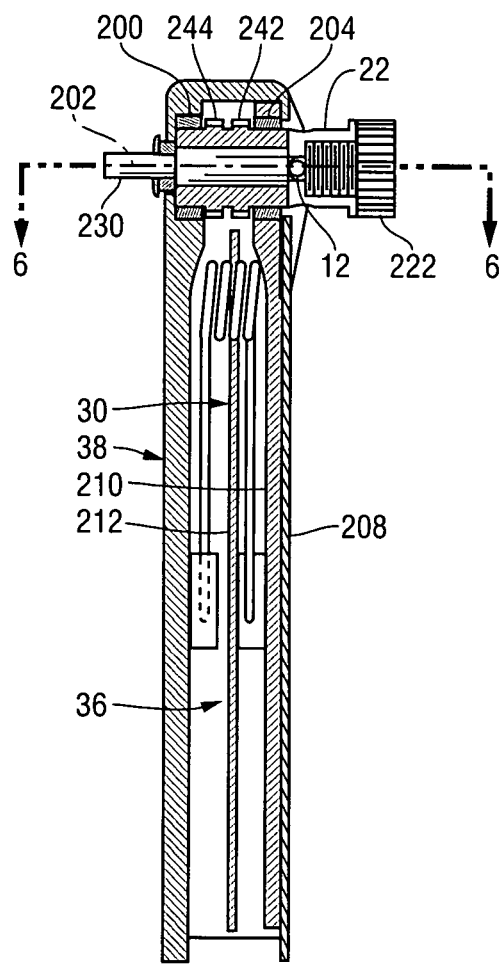
FIG. 5 is a cross-sectional end elevation of a wire puller within the wire apparatus of FIG. 1, shown as indicated by section lines 5-5 therein.

FIG. 5 is a cross-sectional end view of the wire puller 18, showing the handle 30 in the closed position, partly disposed within the opening 36 of the housing 38. The capstan 22 is mounted within a bearing 200 in the housing 38 to rotate about an axis 202, while the handle 30 includes a bearing 204 pivoting on the capstan 22, also about the axis 202. The housing 38 includes a housing frame 206 and a housing cover 208, while the handle 30 includes a handle frame 210 and a handle cover 212.

Figure 6:
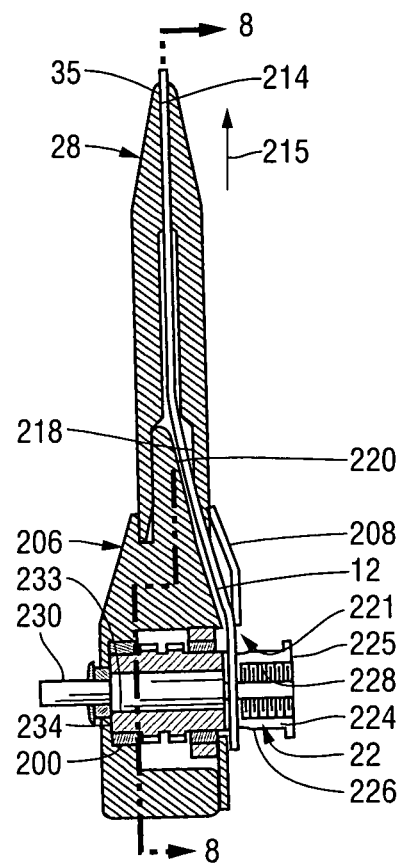
FIG. 6 is a cross-sectional plan view of the wire puller of FIG. 5, taken as indicated by section lines 6-6 in FIG. 5.

FIG. 6 is a cross-sectional plan view of the wire puller 18, taken as indicated by section lines 6-6 in FIG. 5, particularly to show a wire channel 213 forming the path of the surgical wire 12 between a hole 214 in the tip 32 of the elongated tubular member 28 and the capstan 22. The elongated tubular member 28 extends outward in the direction of arrow 215, providing working space around the handle 30 and the housing 38 when the tip 32 is held against the second end portion 122 of a the surgical wire 12, as shown in FIG. 4. The elongated tubular member 28 includes a central hole 216 having an enlarged end 218, into which a deflection wedge 220 extends as part of the housing frame 206, to which the elongated tubular member 28 is attached. The deflection wedge 220 causes the end of the surgical wire 12 to be deflected through a slot 221 between the housing frame 206 and a part of the housing cover 208, toward the capstan 22.

Figure 7:
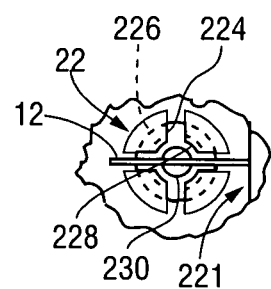
FIG. 7 is a fragmentary side elevation of the wire puller of FIG. 5, showing a capstan therein.

FIG. 7 is a fragmentary side elevation of the wire puller 18, showing the capstan 22. A wire retaining screw 222 (shown in FIG. 5) has been removed in FIGS. 6 and 7 to reveal a slot 224, into which an end of the second end portion 122 of the surgical wire 12 is placed For example, the slot 224 is cruciform in shape, extending into the capstan 22 from an outer end 225. Then, the capstan 22 is driven in the direction of arrow 24 to wind the second end portion 122 onto the drum surface 226 of the capstan 22. Preferably, the wire retaining screw 222, which engages a threaded hole 228 extending along a center of the slot 224, is removed to facilitate the installation of the surgical wire 12 within the slot 224, and is installed to remain within the threaded hole 228 while the surgical wire 12 is wound onto the drum surface 226 to hold the end of the wire 12 in place. An ejection pin 230 is additionally provided for pushing the end of the wire 12 out of the cruciform slot 224 in the axial direction of arrow 232. The ejection pin 230 sides within a hole 233 extending into the capstan 22 from an end 234 thereof, opposite the outer end 225.

Figure 8:
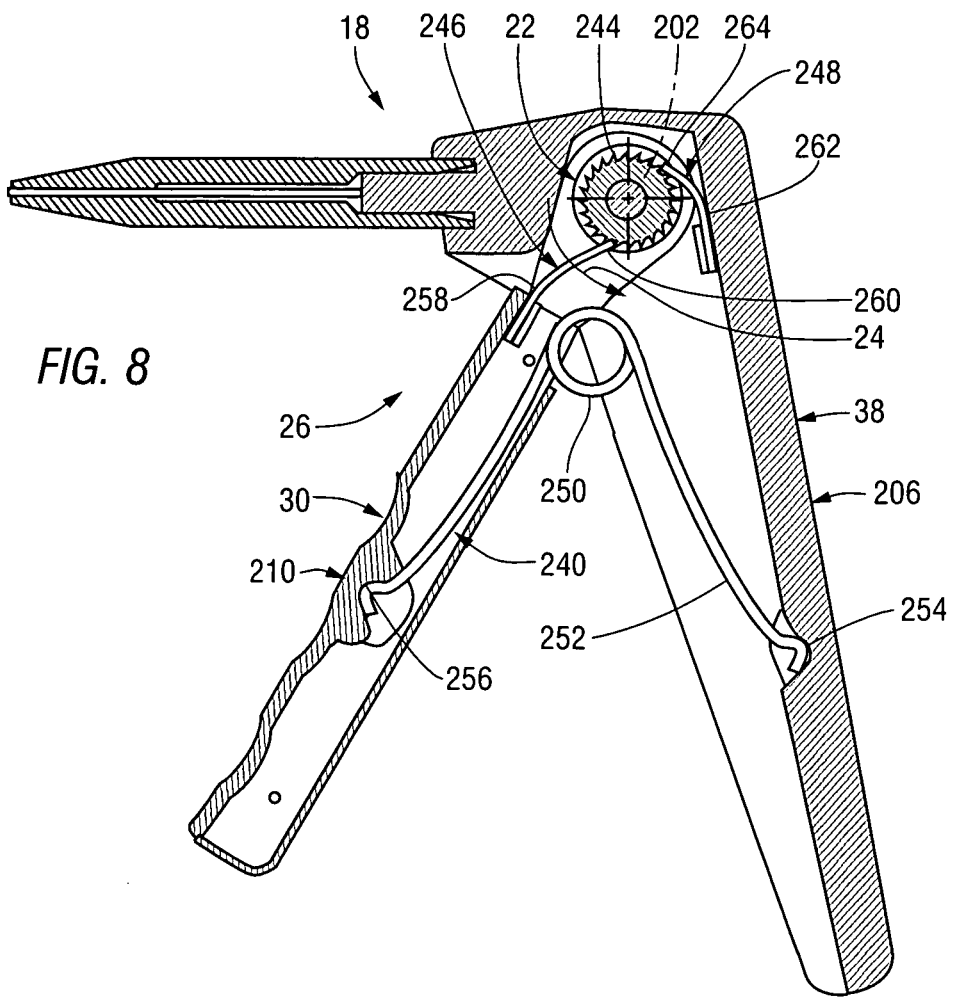
FIG. 8 is a cross-sectional side elevation of the wire puller of FIG. 5, taken as indicated by section lines 8-8 in FIG. 6, with a handle therein shown in an open condition.
Figure 9:
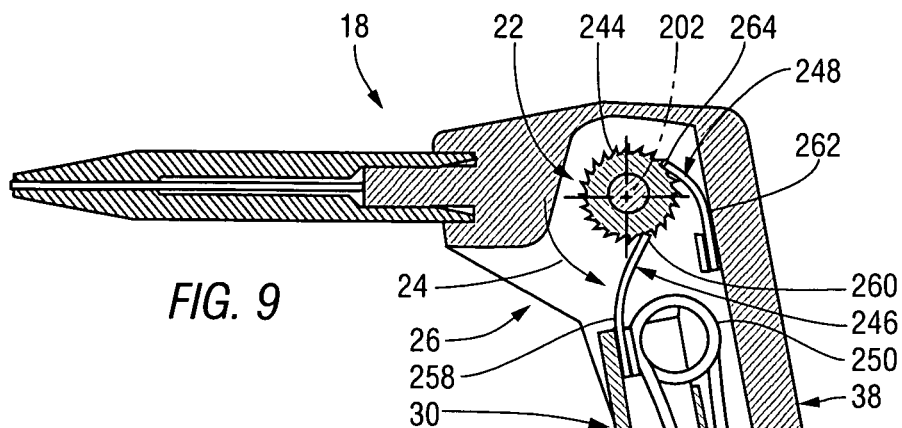
FIG. 9 is a cross-sectional side elevation of the wire puller of FIG. 5, additionally taken as indicated by section lines 8-8 in FIG. 6, with a handle therein shown in a closed condition.

FIGS. 8 and 9 are cross-sectional side elevations of the wire puller 18, each taken as shown be section lines 8=8 in FIG. 6, with the handle 30 being shown in the open position in FIG. 8 and in the closed position in FIG. 9. The capstan drive 26 includes the handle 30, a return spring 240, deployed between the handle 30 and the puller housing 38, a drive ratchet 242 (shown in FIG. 5), a braking ratchet 244, a drive pawl 246, and a braking pawl 248. Both the handle 30 and the capstan 22 are mounted to pivot on the common axis 202 relative to the puller housing 38. The return spring 240 is formed as a torsion spring including a helical portion 250 and a pair of legs 252, each extending to an end 254. The housing frame 206 and the handle frame 210 each include a pocket 256 holding one of he ends 254 of the return spring 240. The ratchets 242, 244 and the capstan 22 are attached to one another, and may be integral portions of a common structure.

The capstan 22 is driven in the forward rotational direction of arrow 24 (It is noted that the direction of arrow a 24 appears counterclockwise in FIG. 1 and clockwise in FIGS. 8 and 9, because these elevations are taken from opposite sides of the wire puller 18) by the engagement of the drive pawl 246 with the drive ratchet 242 as the handle 30 is manually moved in the direction of arrow 24, toward the closed position of FIG. 9 from the open position of FIG. 8. For example, this action is performed by squeezing the wire puller 18 within one hand. The drive pawl 246 is formed as a leaf spring having a proximal end 258 attached to the handle frame 210, and a distal end 260 engaging teeth of the drive ratchet 242 which are oriented so that the sprocket can be driven in the direction of arrow 24. Rotation of the capstan 22 opposite the forward direction of arrow 24 is prevented by the engagement of the braking pawl 248 with the braking ratchet 244, allowing the handle 30 to be returned from the closed position of FIG. 9 to the open position of FIG. 8 by the return spring 240 when the hand holding the handle 30 in the closed position is relaxed. The braking pawl 248 is formed as a leaf spring having a proximal end 262 attached to the housing frame 206 and a distal end 264 engaging teeth of the braking ratchet 244, which are oriented to prevent rotation opposite the direction of arrow 24.

Figure 10:
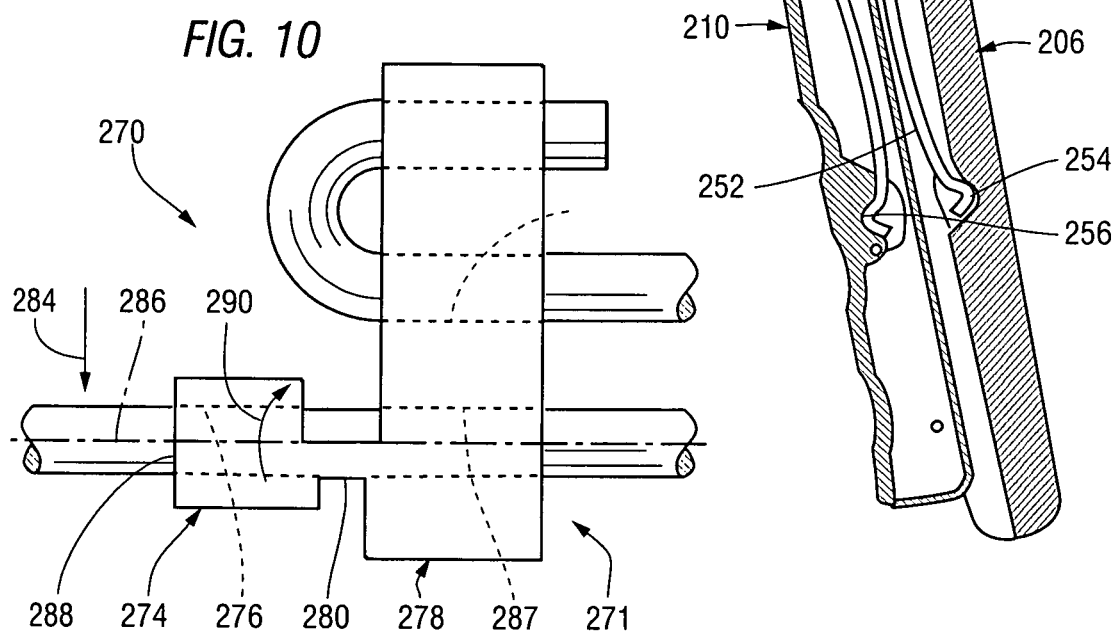
FIG. 10 is a plan view of a wire connector built in accordance with a first alternative embodiment of the invention.

FIG. 10 is a plan view of a wire connector 270 built in accordance with a first alternative embodiment of the invention to include a second receptacle 271 having a locking structure 272 with only one locking member 274, through which a locking hole 276 extends. The locking member 274 is connected to the connector housing 278 by a single flexible member 280, in the form of a beam structure disposed in the transverse direction of arrow 284 from a common axis 286 of the locking hole 276 and a housing hole 287. While the locking structure 272 is shown in an unlocked position, contact between the external puller surface 152 (shown in FIG. 4), and an external locking surface 288 of the locking member 274 causes a moment acting in the direction of arrow 290 to bend the flexible member 280 so that the holes 276, 286 are moved out of alignment with one another, locking the surgical wire 12 in place within the connector 270. Other aspects of the connector 270 are as described above regarding the wire connector 16 in reference to FIGS. 1-4.

Figure 11:
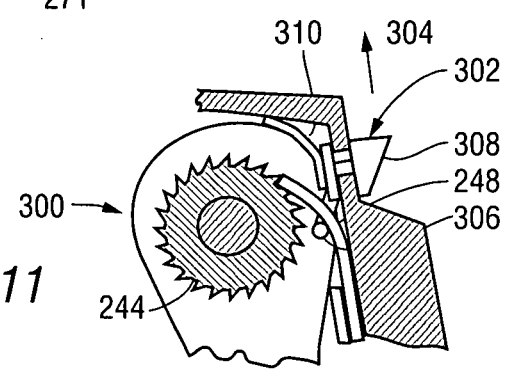
FIG. 11 is a fragmentary cross-sectional side elevation of a wire puller built in accordance with a second alternative embodiment of the invention.

FIG. 11 is a fragmentary cross-sectional elevation of a wire puller 300 built in accordance with a second alternative embodiment of the invention to include a capstan release member 302 that is movable in the direction of arrow 304 between an engaged position, in which it is shown, and a released position. When the capstan release member 302 is in the engaged position, the braking ratchet 244 is engaged, with the braking pawl 248 engaging the braking ratchet 244. When the capstan release member 302 is in the released position, a pin 306, forming part of the capstan release member 302, holds the braking pawl 248 away from the braking ratchet 244, so that the braking ratchet 244 is disengaged, allowing the capstan 22 to turn opposite the forward direction of arrow 24. The capstan release member 302 is moved into the disengaged position by pushing an inclined surface 308 thereof, and is returned into the engaged position by a leaf spring 310 when the inclines surface 308 is released. For example, the capstan 22 may be released to align the wire retaining slot with the wire within the wire channel 213 (shown in FIG. 6) before beginning the process of winding the surgical wire 12 on the capstan 22 and to allow a portion of the wire 12 to be pulled of the capstan 22, so that a space is provided between the wire puller 200 and the wire connector 16 for cutting the wire 12 stretched therebetween.

It is understood that, while various elements and features have been described with some degree of particularity, such descriptions have been given only by way of example, and that many variations are possible within the spirit and scope of the inventions, which is understood to be limited only by the appended claims.

What is claimed is:

1. Apparatus comprising:
   a loop of surgical wire, configured to be wrapped at least one time around an internal body structure,
   a wire connector including a connector housing, a first receptacle configured to accept and hold a first end portion of the loop of surgical wire, and a second receptacle, configured to accent and hold a second end portion of the length of surgical wire, wherein the second receptacle includes a locking structure allowing movement of the second end portion within the second receptacle with the locking structure in an unlocked condition and preventing movement of the second end portion within the second receptacle with the locking structure in a locked condition; and wherein the locking structure includes an external locking surface, wherein external pressure on the external locking surfaces causes the locking structure to change from the unlocked condition to the locked condition, wherein the second receptacle additionally comprises a housing hole having an alignment axis within the connector housing, wherein the locking structure additionally includes an inner locking member having an inner locking hole, an inner flexible structure comprising a beam structure disposed in a transverse direction from the alignment axis, attaching the inner locking member to the connector housing, an outer locking member having an outer locking hole, and an outer flexible structure comprising a beam structure disposed opposite the transverse direction from the alignment axis, attaching the outer locking member to the inner locking member, wherein the flexible structures are deflected to move the locking holes out of alignment with one another and with the housing hole, causing the inner flexible structure and the outer flexible structures to deflect in opposite transverse directions to move the inner and outer locking members transversely in opposite directions, by applying the external pressure to the external locking surface, changing the locking structure from the unlocked condition to the locked condition, and wherein the external locking surface comprises an external surface of the outer locking member, extending around the outer locking hole; and a wire puller, including an external puller surface wherein the wire puller is configured to pull the second end portion extending from the second receptacle of the wire connector, while providing the external pressure on the external locking structure of the wire connector.

2. The apparatus of claim 1, wherein the wire puller includes a puller housing and an elongated tubular member extending outward from the housing, with the external puller surface disposed at an end of the elongated tubular member for receiving the second end portion as a capstan is driven in a forward direction of rotation.

3. The apparatus of claim 2, wherein the wire puller additionally includes:
a capstan configured for winding the second portion as it is pulled from the wire connector and
a capstan drive configured for rotating the capstan with a torque sufficient to push the external puller surface against the external locking surface with a force sufficient to cause the locking structure to change from the unlocked condition to the locked condition.

4. The apparatus of claim 3, wherein the capstan is rotatably mounted on the puller housing, and wherein the capstan drive comprises;
a handle movably attached to the puller housing to move in either direction between an open position and a closed position;
a return spring, moving the handle from the closed position to the open position;
a drive ratchet, attached to the capstan, having teeth oriented to drive the capstan in a forward direction of rotation;
a drive pawl, having a proximal end attached to the handle and a distal end held in contact with the teeth of the drive ratchet,
a braking ratchet, having teeth oriented to restrict rotation of the capstan in a direction opposite the forward direction of rotation, and a braking pawl, having a proximal end attached to the puller housing and a distal end held in contact with the teeth of the braking ratchet.

5. The apparatus of claim 3, additionally comprising a wire channel extending between the hole within the eternal puller surface and the capstan, wherein the capstan includes:
a wire receiving slot extending inward from an outer end of the capstan:
a removable wire retainer extending into the wire receiving slot to hold a wire within the wire receiving slot; and
a wire ejection pin movable into the wire receiving slot to push a wire outward from the wire receiving slot.

6. The apparatus of claim 5, wherein:
the wire receiving slot has a cruciform shape,
the capstan includes a threaded hole extending inward from the outer end and a smooth hole extending inward from an end opposite the outer end,
the removable wire retainer comprises a screw engaging the threaded hole within the capstan; and
the wire ejection pin is mounted to side within the smooth hole in the capstan.

7. The apparatus of claim 5, additionally comprising a capstan release member movable between an engaged position, allowing a distal end of a braking pawl to be held in contact with teeth of a braking ratchet, and a disengaged position, holding the distal end of the braking pawl away from the teeth of the braking ratchet.

8. A wire connector comprising:
a connector housing;
a first receptacle configured to accept and hold a first end portion of a loop of surgical wire, and
a second receptacle, configured to accept and hold a second end portion of the loop of surgical wire, wherein the second receptacle includes a locking structure allowing movement of the second end portion within the second receptacle with the locking structure in an unlocked condition and preventing movement of the second end portion within the second receptacle with the locking structure in a locked condition; and wherein the locking structure includes an external locking surface, wherein external pressure on the external locking surfaces causes the locking structure to channel from the unlocked condition to the locked condition, wherein the second receptacle additionally comprises a housing hole having an alignment axis within the connector housing, and wherein the locking structure additionally includes an inner locking member having an inner locking hole, an inner flexible structure comprising a beam structure disposed in a transverse direction from the alignment axis, attaching the inner locking member to the connector housing, an outer locking member having an outer locking hole, and an outer flexible structure comprising a beam structure disposed opposite the transverse direction from the alignment, axis attaching the outer locking member to the inner locking member, wherein the flexible structures are deflected to move the locking holes out of alignment with one another and with the housing hole, causing the inner flexible structure and the outer flexible structure to deflect in opposite transverse directions to move the inner and outer locking members transversely in opposite directions by applying the external pressure to the external locking surface, changing the locking structure from the unlocked condition to the locked condition, and wherein the external locking surface comprises an external surface of the outer locking member, extending around the outer locking hole.

9. The wire connector of claim 8, wherein the first receptacle comprises a pair of holes extending through the connector housing.

* * * * *